United States Patent [19]

Edington et al.

[11] 4,243,808
[45] Jan. 6, 1981

[54] 4-PYRIDINAMINE DERIVATIVES

[75] Inventors: Edwin T. Edington, Cookham; Alan C. White, Windsor, both of England

[73] Assignee: John Wyeth & Brother Limited, Taplow, England

[21] Appl. No.: 51,076

[22] Filed: Jun. 22, 1979

Related U.S. Application Data

[63] Continuation-in-part of Ser. No. 873,192, Jan. 30, 1978, Pat. No. 4,180,670.

[30] Foreign Application Priority Data

Feb. 2, 1977 [GB] United Kingdom ................. 4354/77
Jul. 9, 1977 [GB] United Kingdom ............... 28879/77

[51] Int. Cl.$^3$ ............................................ C07D 213/38
[52] U.S. Cl. ..................................... 546/285; 424/263
[58] Field of Search ................................ 546/285, 270

[56] References Cited

U.S. PATENT DOCUMENTS 3,313,822  4/1967  Meltzer ................................. 546/329

OTHER PUBLICATIONS

Sokov, Chem. Abstracts, vol. 35, 25104 (1941).
Kaye et al., Journal of Amer. Chem. Soc., vol. 74, pp. 403–407 (1952).
Villani et al., Journal of the Amer. Chem. Soc., vol. 73, pp. 5916–5917 (1951).
Carpenedo et al., Chem. Abstracts, vol. 73, p. 236, 108061s (1970).
Mndzhoyan et al., Chem. Abstracts, vol. 52, 4641b (1958).

Primary Examiner—Alan L. Rotman
Attorney, Agent, or Firm—Arthur E. Wilfond

[57] ABSTRACT

Novel 4-pyridinamine derivatives having the formula

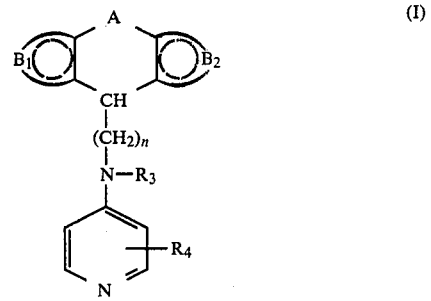

(I)

and their pharmaceutically acceptable acid addition salts (wherein A is $C_1$ to $C_4$ alkylene, each of $B_1$ and $B_2$, together with the two carbon atoms joined thereto, forms arylene or heteroarylene, $R_3$ and $R_4$ are independently hydrogen or lower alkyl and n is 0 or 1) are described. They show CNS activity and may be used as anti-depressant drugs.

3 Claims, No Drawings

4-PYRIDINAMINE DERIVATIVES

This application is a continuation-in-part of Patent Application Ser. No. 873,192 filed Jan. 30, 1978, now U.S. Pat. No. 4,180,670, in the names of Edwin Trevor Edington and Alan Chapman White entitled "NOVEL PYRIDINE DERIVATIVES".

The invention relates to novel 4-aminopyridine derivatives which show pharmaceutical activity, particularly CNS activity.

The invention provides novel compounds having the formula

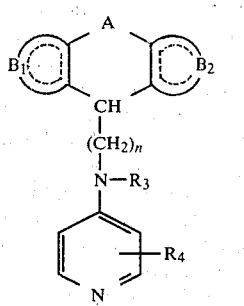 (I)

and their pharmaceutically acceptable acid addition salts, wherein A is alkylene of 1 to 4 carbon atoms, each of $B_1$ and $B_2$ together with the two carbon atoms attached thereto independently represents arylene or heteroarylene, $R_3$ and $R_4$ are independently hydrogen or lower alkyl and n is 0 or 1, preferably 0.

The dotted lines in formula I in the rings including $B_1$ and $B_2$ are intended to indicate the aromatic character of the rings. The arylene and heteroarylene groups may be phenylene; phenylene substituted by one to two substituents selected from lower alkyl, lower alkoxy, lower alkylenedioxy, halogen and trifluoromethyl; naphthylene; pyridine-diyl and thiophene-diyl.

By the term "lower" as used herein in connection with such groups alkyl, alkoxy and alkylenedioxy, there is meant that the group contains up to 6 carbon atoms, preferably up to 4 carbon atoms. By the term "arylene or heteroarylene" there is meant a divalent group of aromatic characters, for instance, ortho-phenylene, substituted o-phenylene, thiophene-2,3-diyl or thiophene-3,4-diyl.

The alkylene group of 1 to 4 carbon atoms represented by A in formula I may be a straight chain, for instance, methylene, dimethylene or trimethylene or may be branched, for example a group having the formula —C(CH$_3$)$_2$—CH$_2$—.

$R_3$ and $R_4$ may be the same or different and are selected from hydrogen and lower alkyl, for example, methyl, ethyl, propyl and butyl. $R_3$ and $R_4$ are preferably chosen from hydrogen and methyl.

The symbol n preferably represents 0.

The acid addition salts may be formed from inorganic acids and organic acids and examples include the sulphate, hydrochloride, hydrobromide, hydroiodide, nitrate, phosphate, sulphonate (such as the methane sulphonate and toluene-p-sulphonate), acetate, maleate, fumarate, tartrate and formate.

It will be apparent to the reader that some of the compounds having formula I possess an asymmetric carbon atom and thus exhibit the property of optical isomerism. The invention includes the individual optical isomers as well as the racemic mixtures. The racemates may be resolved into individual optical isomers in known manner.

The compounds of general formula I and their acid addition salts can be prepared in a number of ways by building up the molecule from suitable starting materials in known manner. A choice of methods exists so that the most appropriate one may be chosen in each case. In particular the compounds may be prepared by reduction of amides, conversion of primary amines into secondary amines or conversion of secondary amines into tertiary amines and by reduction of Schiff's bases.

The invention provides a process for the preparation of a compound having formula I or a pharmaceutically acceptable acid addition salt thereof, wherein (a) an amine having the formula II

 (II)

or a salt thereof, is reacted with a compound having formula III

Y-Z (III)

(where Z is a replaceable atom or group) to form an amine having the formula IV

 (IV)

as a free base or acid addition salt (where in formulae III, IV and V any one of W, X and Y represents a group having the formula V

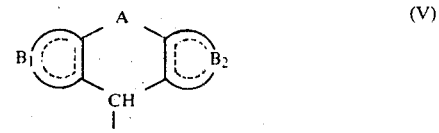 (V)

(where A, $B_1$ and $B_2$ are as defined above), another one of W, X and Y represents a group having the formula VI

 (VI)

(where $R_4$ is defined above) and the remaining one of W, X and Y represents $R_3$ as defined above subject to the proviso that, when Y represents $R_3$ as defined above, then $R_3$ is lower alkyl); or (b) a Schiff's base having the formula VII or VIII

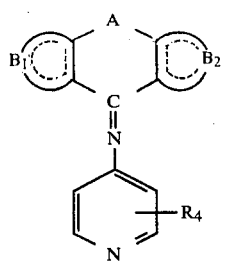

or

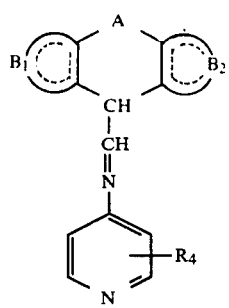

(wherein A, $B_1$, $B_2$ and $R_4$ are as defined above) is reduced; or (c) an amide having the formula IX

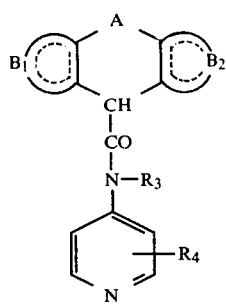

or an acid addition salt thereof (wherein A, $B_1$, $B_2$, $R_3$ and $R_4$ are as defined above) is reduced to form a compound where n is 1. Where desired, the process may include conversion of a free base form of the compound having formula I into a pharmaceutically acceptable acid addition salt thereof or conversion of an acid addition salt form of a compound having formula I into its free base form.

The starting materials for method (a), namely those having formulae II and III are sometimes known and, where new, can be prepared in known manner. The compounds having general formula IX and their acid addition salts are new compounds also provided by the invention. They can be prepared in manner known per se. In particular an amine having the formula

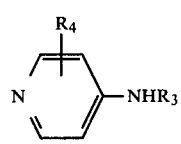

(where $R_3$ and $R_4$ are as defined above) is acylated to introduce the acyl group

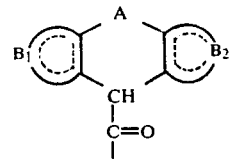

(where A, $B_1$ and $B_2$ are as defined above). The acylation may be performed using the acyl halide, for instance, the acyl chloride or acyl bromide, in the presence of a suitable base. The Schiff's bases of formulae VII and VIII are obtainable in known manner.

Method (a) can be carried out using known procedures for converting primary amine into secondary amines and secondary amines into tertiary amines. We prefer to use a compound of formula III in which Z is halogen, particularly bromine or chlorine.

The starting amine may be used as such or in the form of a salt thereof, for instance, the lithium salt. The lithium salt is treated with a lower alkyl halide, for example, methyl iodide or ethyl bromide, to effect alkylation to result in a tertiary amine in which $R_3$ is lower alkyl.

Method (a) may also be used to form secondary amines. For example a compound having the formula

W-NH$_2$ may be treated with a compound having formula Y-Z (where one of W and Y represents a group having formula V and the other represents a group having formula VI) to form a secondary amine of formula W-NH-Y. We prefer to carry out this method by reacting an appropriately substituted methyl halide of formula XII

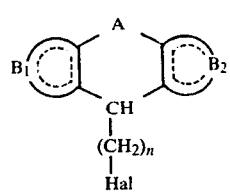

(where Hal is halogen such as chlorine or bromine and n is 0 or 1) with 4-pyridinamine or its 2-or 3-lower alkyl derivative.

The reaction of the amine having formula II with the compound having formula III may be carried out under elevated temperature in a suitable solvent, for example, toluene.

The reduction according to method (b) may be carried out under conditions known for the reduction of Schiff's bases to form amines. As reducing agent there may be used lithium aluminum hydride or sodium borohydride. In particular, the reduction may be performed using sodium borohydride in an alcohol, for instance, methanol or ethanol, at room temperature. The reduction may also be carried out using lithium aluminium hydride in ether at room temperature or under reflux. Catalytic hydrogenation may be used. The reduction conditions employed should be so chosen as to avoid reduction of the pyridine ring and/or cleavage of the tricyclic group.

It will be appreciated that the reduction products obtained from Schiff's bases of formula VII are compounds where n is 0 and $R_3$ is hydrogen and those obtained from Schiff's bases of formula VIII are cmpounds where n is 1 and $R_3$ is hydrogen.

The reduction according to method (c) may be carried out under conditions known for the reduction of amides to form amines. As reducing agent there may be used lithium aluminium hydride or diborane. It will be appreciated that the reduction products obtained are compounds where n is 1.

When a product of formula I has been prepared in the form of its free base this may be converted into an acid addition salt by addition of an acid. For example, ethereal hydrogen bromide or ethereal hydrogen chloride may be added to a solution of the free base to give the hydrobromide or hydrochloride salt respectively. Acid addition salt forms of compounds having formula I may be converted into the free base form in known manner, in particular, by addition of a base.

The compounds having formula I and their pharmaceutically acceptable acid addition salts are indicated for pharmaceutical use. In particular they show CNS (central nervous system) activity, when tested on warm blooded animals. They reverse the hypothermia induced by reserpine on mice and thus may have potential use as antidepressant drugs.

The reserpine hypothermia test can be carried out by the following procedure:

Groups of 10 female mice (21 to 25 g) are dosed with reserpine, 2.5 mg/kg s.c. The mice are placed in cages without sawdust but with food and water at 18° C. After 17 hours (overnight) the rectal temperature of each mouse is measured with a thermocouple inserted to a standard depth of 2 cm. The mice are then challenged with compounds at graded dose levels either orally or intraperitoneally. The rectal temperature is measured hourly for six hours or until a maximum rise in temperature is achieved whichever is the shorter. A control group is run. The rise in rectal temperature caused by the drug is compared with that in the control group.

The compound of Example 1 was active in this procedure at 5 mg/kg p.o. and the compound of Example 2 was active at 100 mg/kg p.o. The compound of Example 1 was also equipotent with imipramine in blocking the uptake of noradrenaline in rat brain slices in vivo, another test indicative of antidepressant activity.

The invention also includes pharmaceutical compositions containing as active ingredient a compound of formula I or a pharmaceutically acceptable acid addition salt thereof which may be micronised if desired. In addition to the active ingredient said compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80%, by weight of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with an encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, a sterile organic solvent or a mixture of both. Preferably a liquid carrier is one suitable for parenteral injection. Where the active ingredient is sufficiently soluble it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example, packet powders or vials or ampoules. The unit dosage form can be a capsule, cachet or tablet itself, or it can be the appropriate number of any of these in package form. The quantity of active ingredients in a unit dose of composition may be varied or adjusted from 5 mg or less to 500 or more, according to the particular need and the activity of the active ingredient. The invention also includes the compounds in the absence of carrier where the compounds are in unit dosage form.

The following Examples illustrate the invention:

EXAMPLE 1

N-(10,11-dihydro-5H-dibenzo[a,d]cyclohepten-5-yl)-4-pyridinamine 10.3 Grams (45 millimoles) of 5-chloro-10,11-dihydro-5H-dibenzo[a,d]cycloheptene and 7.05 grams (75 millimoles) of 4-aminopyridine were heated together in 150 cc of dry toluene under reflux for 24 hours. After cooling, the toluene solution was decanted, washed twice with 75 cc of water and then washed twice with 2 N hydrochloric acid (50 cc each time). A solid then precipitated at the interface. This solid (A) was collected and amounted to 1.42 grams. A gum also precipitated on the vessel walls, and was separated from the toluene and aqueous phases, which contained only unreacted starting materials. This gum was washed with 2 N hydrochloric acid and was then dissolved in chloroform, dried (MgSO$_4$), and evaporated, leaving 1.34 grams of a foam. Extraction of this foam with a little chloroform left 1.0 gram of an insoluble solid (B).

Solid (B) was crystallised from ethyl acetate methanol, giving 0.58 grams of (N-10,11-dihydro-5H-dibenzo[a,d]cyclohepten-5-yl-4-pyridinamine)hydrochloride as colourless crystals, melting point 267°–8°.

Analysis: Found C, 74.7%; H, 6.2%; N, 8.4%. $C_{20}H_{18}N_2 \cdot HCl$ requires C, 74.4% H, 5.9%; N, 8.7%.

Further less pure material (0.77 grams) of melting point 263°–4° was obtained by crystallisation of solid (A) from ethyl acetate-methanol.

EXAMPLE 2

N-[(10,11-dihydro-5H-dibenzo[a,d]-cyclohepten-5-yl) methyl]-4-pyridinamine

Diborane was generated by the dropwise addition over 1½ hours at room temperature of a solution of 1.14 grams (30 millimoles) of sodium borohydride in 30 cc. of dry diglyme to a mixture of 6.2 cc. (7.1 grams, 50 millimoles) of redistilled boron trifluoride etherate and 6.2 cc of dry diglyme. The evolved diborane was swept in a slow stream of dry nitrogen into a solution of 3.14 grams (10 millimoles) of N-[(10,11-dihydro-5H-dibenzo[a,d]cyclohepten-5-yl)carbonyl]-4-pyridinamine in 50 cc. of dry tetrahydrofuran, cooled in ice. After complete addition of the borohydride solution, the generator flask was heated to 70°–80° for ½ hour to complete the generation of diborane, which was swept into the reduction mixture as before. The reduction mixture was stirred at 0° for a further hour and was then heated to reflux for 3 hours, maintaining the nitrogen atmosphere. The apparatus was then sealed and allowed to cool overnight. 5 Milliliters of 6 N hydrochloric acid were then added dropwise with care to the reduction mixture, resulting in vigorous hydrogen evolution. The acid solution was then evaporated to dryness to remove tetrahydrofuran and the residue was treated with 25 cc. of water, basified to pH9 with potassium carbonate, filtered, and the filtrate was extracted repeatedly with dichloromethane. The combined organic extracts were dried using $MgSO_4$ and evaporated, leaving 3.02 grams of a yellow oil whose IR spectrum contained no C=0 absorption. This oil was taken up in a mixture of propan-2-ol, methanol and dichloromethane, made acid with ethereal hydrogen chloride, filtered and concentrated to 15 cc. On cooling N-[(10,11-dihydro-5H-dibenzo[a,b]cyclohepten-5-yl)methyl]-4-pyridinamine, hydrochloride was deposited as colourless crystals (1.56 g, 42%), mp 245°–6° with effervescence.

Analysis Found: C, 75.0%; H, 6.3%; N, 8.1%. $C_{21}H_{20}N_2 \cdot HCl$ requires C, 74.9%; H, 6.3%; N, 8.3%.

The N-[(10,11-dihydro-5H-dibenzo[a,d]cyclohepten-5-yl)carbonyl]-4-pyridinamine starting material was prepared as follows:

A solution of 4.7 grams (50 millimoles) of 4-aminopyridine in 50 cc. of dry pyridine was treated dropwise at room temperature with a solution of 6.6 grams of 10,11-dihydro-5H-dibenzo[a,d]cyclohepten-5-ylcarbonyl chloride (M. A. Davis, Stanley O. Winthrop, J. Steward, F. A. Sunahara and F. Herr, J. Medicin. Chem. 1963, 6, 251–5) in 50 cc of toluene. After the exothermic reaction subsided the mixture was stirred at room temperature for 4 hours and was then poured into 30 cc of water. 100 milliliters of toluene were added and the phases were separated. The toluene phase was washed once with 100 cc of water, then the combined aqueous phases were back-extracted with toluene (3×100 cc). The combined toluene solutions were dried ($MgSO_4$) and evaporated, leaving an oily residue which was evaporated several times with further toluene and finally once with ethanol to remove residual pyridine, giving 8.45 grams of a yellow solid. This solid was crystallised from toluene (charcoal) giving off-white crystals (4.78 g, 61%), mp 145°–6°; second crop; off-white crystals (0.96 g, 12%), mp 145°–7.5°.

Both crops were indicated by infrared spectroscopy to contain a trace of carboxylic acid (C=0 at 1700 cm), so both fractions were combined, dissolved in toluene (150 cc) and washed with 2 N sodium hydroxide solution (3×25 cc) water (3×25 cc) and saturated sodium chloride solution (2×25 cc) and dried ($MgSO_4$). The solution was filtered, concentrated to 50 cc, and allowed to crystallise, giving 4.64 grams (57% yield) of N-[(10,11-dihydro-5H-dibenzo[a,d]cyclohepten-5-yl)carbonyl]-4-pyridinamine as colourless crystals, mp 148°–9°.

Analysis Found: C, 80.5%; H, 6.0%; N, 9.0%. $C_{21}H_{18}N_2O$ requires C, 80.2%; H, 5.8%; N, 8.9%.

EXAMPLE 3

N-(10,11-dihydro-5H-dibenzo[a,d]-cyclohepten-5-yl)-2-methyl-4-pyridinamine

The title compound is prepared in a similar manner to Example 1 by using 4-amino-2-methylpyridine in place of 4-aminopyridine.

EXAMPLE 4

N-(10,11-dihydro-5H-dibenzo[a,d]-cyclohepten-5-yl)-N-methyl-4-pyridinamine

A solution of 0.01 mole of N-(10,11-dihydro-5H-dibenzo[a,d]-cyclohepten-5-yl)-4-pyridinamine in 100 milliliters of dry tetrahydrofuran is added at −10° C. to a solution of lithium diisopropylamide (prepared from 1.5 milliliters (0.01 mole) of diisopropylamine and butyl lithium in hexane (7.7 milliliters; 0.01 mole) at −20° C.) in 100 milliliters of tetrahydrofuran, in an atmosphere of nitrogen. The solution is stirred at room temperature for 30 minutes and then treated with 0.63 milliliters (0.01 mole) of methyl iodide and stirred at room temperature overnight. The solution is decomposed with 5 milliliters of water and evaporated and the residue is dissolved in propan-2-ol. Acidification with ethereal hydrogen chloride followed by careful addition of ether gives the title compound in hydrochloride form.

EXAMPLE 5

By reacting the following halogen compounds with 4-aminopyridine in a similar manner to Example 1, the following products are obtained.

| Halogen Compound | Product |
| --- | --- |
| 12-chloro-5,6,7,12-tetrahydro-dibenzo[a,d]cyclooctene | N-[5,6,7,12-tetrahydro-dibenzo[a,d]-cycloocten-12-yl]-4-pyridinamine |
| 5-Chloro-10,11-dihydro-1-methyl-5H-dibenzo[a,d]cycloheptene | N-(10,11-dihydro-1-methyl-5H-dibenzo[a,d]cyclohepten-5-yl)-4-pyridinamine |
| 5-Chloro-10,11-dihydro-2,3-dimethoxy-5H-dibenzo[a,d]-cycloheptene | N-(10,11-dihydro-2,3-dimethoxy-5H-dibenzo[a,d]-cyclohepten-5-yl)-4-pyridinamine |
| 2,5-Dichloro-10,11-dihydro-5H-dibenzo[a,d]cycloheptene | N-(2-chloro-10,11-dihydro-5H-dibenzo[a,d]cyclohepten-5-yl)-4-pyridinamine |
| 5-Chloro-3-fluoro-10,11-dihydro-5H-benzo[a,d]cycloheptene | N-(3-fluoro-10,11-dihydro-5H-benzo[a,d]cyclohepten-5-yl)-4-pyridinamine |
| 5-Bromo-10,11-dihydro-10,10-dimethyl-5H-benzo[a,d]cycloheptene | N-(10,11-dihydro-10,10-dimethyl-5H-benzo[a,d]cyclohepten-5-yl)-4-pyridinamine |
| 5-Chloro-10,11-dihydro-3- | N-(10,11-dihydro-3- |

| Halogen Compound | Product |
|---|---|
| trifluoromethyl-5H-benzo[a,d]-cycloheptene | trifluoromethyl-5H-benzo-[a,d]cyclohepten-5-yl)-4-pyridinamine |
| 5-Chloro-10,11-dighydro-2-methoxy-8-methyl-5H-benzo-[a,d]cycloheptene | N-(10,11-dihydro-2-methoxy-8-methyl-5H-benzo[a,d]-cyclohepten-5-yl)-4-pyridinamine |
| 5-Chloro-10,11-dihydro-2,3-methylenedioxy-5H-benzo[a,d]-cycloheptene | N-(10,11-dihydro-2,3-methylene-dioxy-5H-benzo[a,d]cyclohepten-5-yl)-4-pyridinamine |
| 9-Chloro-4,9-dihydro-naphtho-[2,3-c]thiophene | N-(4,9-dihydro-naphtho[2,3-c]thien-9-yl)-4-pyridinamine |
| 10-Chloro-5,10-dihydro-benzo[g]quinoline | N-(5,10-dihydro[g]-quinol-10-yl)-4-pyridinamine |
| 5-Chloro-5-10-dihydro benz[g]isoquinoline | N-(5,10-dihydro-benz[g]-isoquinol-5-yl)-4-pyridinamine |
| 7-Chloro-7,12-dihydro-benz[a]anthracene | N-(7,12-dihydro-benz[a]-anthracen-7-yl)-4-pyridinamine |

We claim:

1. A compound selected from these having the formula

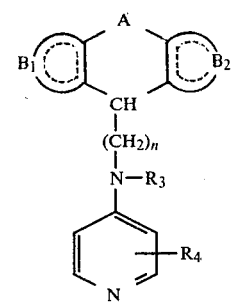

and their pharmaceutically acceptable acid addition salts, wherein A is alkylene of 2 to 3 carbon atoms, each of $B_1$ and $B_2$ together with the two carbon atoms attached thereto independently represents a member selected from the group consisting of phenylene; phenylene substituted by one or two substituents selected from lower alkyl, lower alkoxy, lower alkylenedioxy, halogen and trifluoromethyl; $R_3$ and $R_4$ are independently selected from hydrogen and lower alkyl and n is selected from 0 to 1.

2. A compound as defined in claim 1, which is selected from N-(10,11-dihydro-5H-dibenzo[a,d]cyclohepten-5-yl)-4-pyridinamine and its pharmaceutically acceptable acid addition salts.

3. A compound as defined in claim 1, which is selected from N-[(10,11-dihydro-5H-dibenzo[a,d]cyclohepten-5-yl)methyl]-4-pyridinamine and its pharmaceutically acceptable acid addition salts.

* * * * *